(12) United States Patent
Kim et al.

(10) Patent No.: US 7,809,426 B2
(45) Date of Patent: Oct. 5, 2010

(54) ACQUIRING CONTRAST-ENHANCED, T1 WEIGHTED, CINE MAGNETIC RESONANCE IMAGES

(75) Inventors: Jae Koul Kim, Tucson, AZ (US); Kevin K'O Wen Chen, Singapore (SG); Arthur E. Stillman, Chagrin Falls, OH (US); Ralf B. Loeffler, Cleveland Heights, OH (US); Randolph M. Setser, Cleveland, OH (US); Richard D. White, Chagrin Falls, OH (US)

(73) Assignees: The Cleveland Clinic Foundation, Cleveland, OH (US); Singapore General Hospital Pte Ltd., Singapore (SG); Siemens Medical Solutions USA, Inc., Malvern, PA (US)

( * ) Notice: Subject to any disclaimer, the term of this patent is extended or adjusted under 35 U.S.C. 154(b) by 1069 days.

(21) Appl. No.: 10/835,849

(22) Filed: Apr. 29, 2004

(65) Prior Publication Data

US 2005/0245812 A1    Nov. 3, 2005

(51) Int. Cl.
*A61B 5/05* (2006.01)
(52) U.S. Cl. .................. 600/420; 600/407; 600/410
(58) Field of Classification Search .................. 600/420
See application file for complete search history.

(56) References Cited

U.S. PATENT DOCUMENTS

| | | | | |
|---|---|---|---|---|
| 4,982,328 | A | * | 1/1991 | Kasugai ..................... 600/410 |
| 5,321,357 | A | * | 6/1994 | Maryanski et al. .......... 324/300 |
| 6,205,349 | B1 | * | 3/2001 | Kim et al. .................... 600/420 |
| 6,339,332 | B1 | * | 1/2002 | Deimling ..................... 324/309 |
| 7,412,277 | B1 | * | 8/2008 | Saranathan et al. ......... 600/413 |
| 2004/0049106 | A1 | * | 3/2004 | Kanazawa ................... 600/410 |

OTHER PUBLICATIONS

Kim, R.J., et. al. "The Use of contrast-enhanced magnetic resonance imaging to identify reversible myocardial dysfunction,", The New England Journal of Medicine, Nov. 16, 2000., pp. 1445-1453.*

(Continued)

*Primary Examiner*—Brian Casler
*Assistant Examiner*—James Kish
(74) *Attorney, Agent, or Firm*—Schiff Hardin LLP

(57) ABSTRACT

A method of magnetic resonance imaging of anatomy that is subject to a movement cycle (e.g., the heart during a cardiac cycle), comprising: administering a magnetic resonance contrast agent; waiting a period of time until the contrast agent is effective to cause selected portions of the anatomy (e.g., macrotic cardiac tissue) to have a different T1 recovery rate from that of other portions (normal cardiac tissue); administering a plurality of inversion recovery pulses spaced in time; acquiring image data at a data acquisition time that is spaced in time by a known time interval following an inversion recovery pulse; varying the time within the movement cycle at which the inversion recovery pulses are administered so that the associated data acquisition times are at a plurality of phases of the movement cycle; processing image data acquired at a phase of the movement cycle to produce at least a portion of an image frame at that phase; and performing the processing for a plurality of phases of the movement cycle to produce a plurality of image frames corresponding to a plurality of phases 29 Claims, 11 Drawing Sheets

OTHER PUBLICATIONS

Haacke, E.M. et. al., Magnetic Resonance Imaging, Physical Principles and Sequence Design, Wiley-Liss, 1999, p. 416.*

Sodickson, D. K. et. al., "Breaking the speed limit in magnetic resonance imaging: an introduction to parallel MRI," Proceedings of the joint embs/bmes conference, Houston, TX., Oct. 23-26, 2002, pp. 1173-1174.*

Westbrook, C. et. al., MRI in Practice, Blackwell Scientific Publications, 1993, pp. 67-74, 192, 200-202.*

Thornhill et al., "The assessment of myocardial viability: a review of current diagnostic imaging approaches," J. Cardiovasc. Magn. Reson. 4:381-410 (2002).

Sandstede, "Assessment of myocardial viability by MR imaging," Eur. Radiol. 13:52-61 (2003).

Simonetti et al., "An improved MR imaging technique for the visualization of myocardial infarction," Radiology 218:215-223 (2001).

Kim et al., "Relationship of MRI delayed contrast enhancement to irreversible injury, infarct age, and contractile function," Circulation 100:1992-2002 (1999).

Wagner et al., "Contrast-enhanced MRI and routine single photon emission computed tomography (SPECT) perfusion imaging for detection of subendocardial myocardial infarcts: an imaging study," Lancet 361:374-379 (2003).

Klein et al., "Assessment of myocardial viability with contrast-enhanced magnetic resonance imaging—comparison with positron emission tomography," Circulation 105: 162-167 (2002).

Kellman et al., "Phase-sensitive inversion recovery for detecting myocardial infarction using gadolinium-delayed hyperenhancement," Magn. Reson. Med. 47:372-83 (2002).

Griswold et al., "Generalized autocalibrating partially parallel acquisitions (GRAPPA)," Magn. Reson. Med. 47:1202-1210 (2002).

* cited by examiner

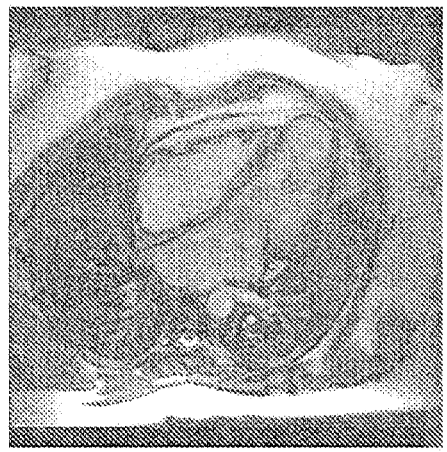
FIG. 2A  CINE TRUEFISP END SYSTOLE ("PRIOR ART")
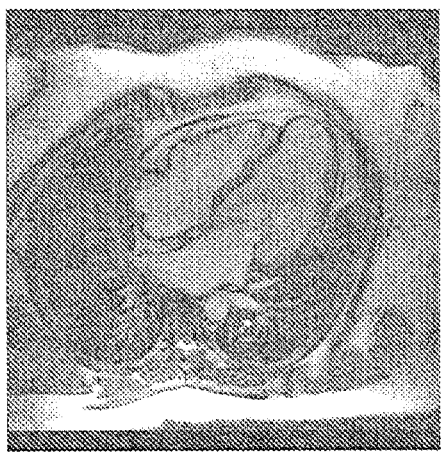
FIG. 2B  CINE TRUEFISP LATE DIASTOLE ("PRIOR ART")
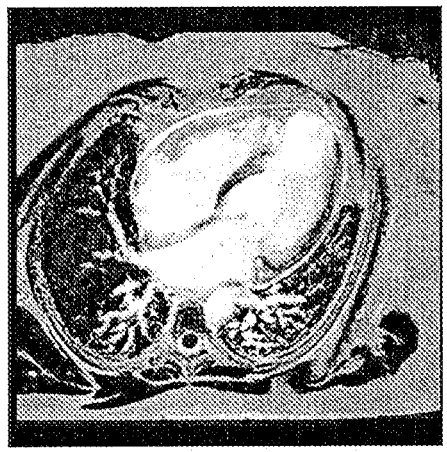
FIG. 2C  DELAYED ENHANCEMENT LATE DIASTOLE ("PRIOR ART")

SCAR-CINE END SYSTOLE

SCAR-CINE LATE DIASTOLE

CINE TRUEFISP END SYSTOLE ("PRIOR ART")

CINE TRUEFISP LATE DIASTOLE ("PRIOR ART")

DELAYED ENHANCEMENT LATE DIASTOLE ("PRIOR ART")

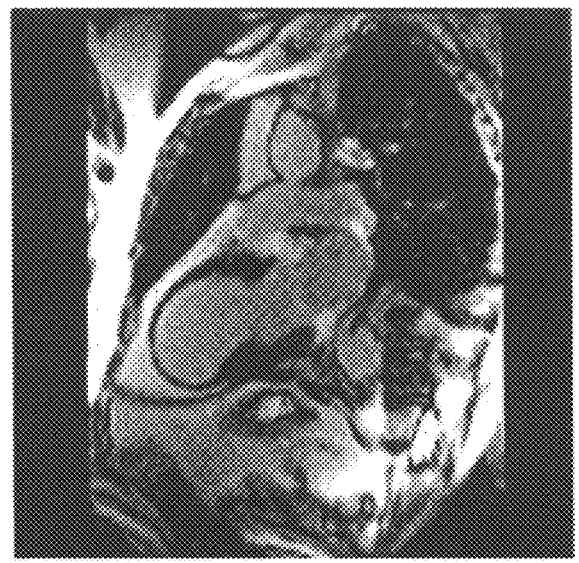
FIG. 3D  SCAR-CINE END SYSTOLE
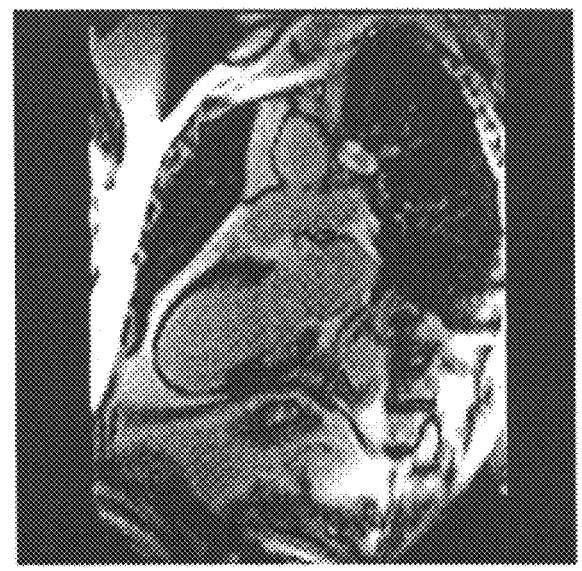
FIG. 3E  SCAR-CINE LATE DIASTOLE

CINE TRUEFISP END SYSTOLE ("PRIOR ART")

CINE TRUEFISP LATE DIASTOLE ("PRIOR ART")

DELAYED ENHANCEMENT LATE DIASTOLE ("PRIOR ART")

SCAR-CINE END SYSTOLE

SCAR-CINE LATE DIASTOLE

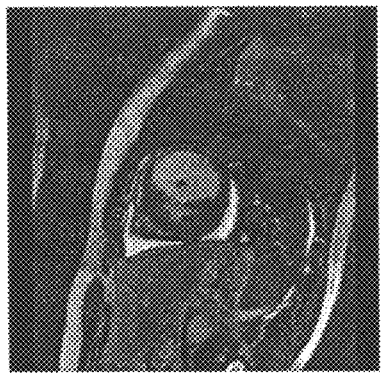
FIG. 5A EARLY DIASTOLE IMAGE 1
FIG. 5B LATE DIASTOLE
FIG. 5C LATE SYSTOLE

FIG. 5D  EARLY DIASTOLE IMAGE 1
FIG. 5E  LATE DIASTOLE
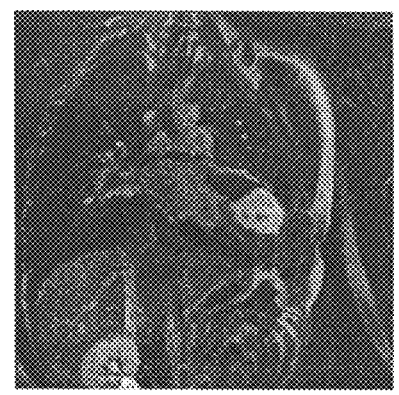
FIG. 5F  LATE SYSTOLE

ACQUIRING CONTRAST-ENHANCED, T1 WEIGHTED, CINE MAGNETIC RESONANCE IMAGES

TECHNICAL FIELD

This invention relates to magnetic resonance (MR) imaging, and more particularly to cardiac MR imaging.

BACKGROUND

The identification of viable myocardium is an important, common clinical goal, e.g., in the evaluation of patients with chronic ischemic disease for possible revascularization therapy (Thornhill et al., "The assessment of myocardial viability: a review of current diagnostic imaging approaches," J. Cardiovase. Magn. Reson. 4:381-410 (2002)). Viability imaging refers to imaging techniques that identify abnormal myocardium which could potentially recover function after reperfusion (viable myocardium). Magnetic resonance imaging (MRI) is increasingly used to identify viable myocardium (Sandstede, "Assessment of myocardial viability by MR imaging," Eur. Radiol. 13:52-61 (2003)). The standard MRI evaluation is based on a comparison of separately acquired images of the left ventricle—a delayed enhancement MRI (DE-MRI) image and a set of cine-MRI image frames. The cine-MRI image frames provide information on whether the myocardium is moving abnormally. But, abnormal motion can be the result of tissue that is chronically infarcted (non-viable) myocardium that is being passively moved, or abnormally contracting myocardium (viable) that could potentially recover function after revascularization. The DE-MRI image highlights chronic scar with bright signal, helping to determine non-viable myocardium from viable myocardium.

The delayed enhancement MRI (DE-MRI) image is typically acquired in the diastolic phase (when little heart motion occurs) at a delayed time after injection of a contrast agent (e.g., gadolinium chelate) and is typically acquired as a single two dimensional (2D) slice. DE-MRI uses an inversion recovery (IR) pulse to null normal myocardial signal (Simonetti et al., "An improved MR imaging technique for the visualization of myocardial infarction," Radiology 218:215-223 (2001)). This creates a tissue contrast where non-viable myocardium usually appears bright (Kim et al., "Relationship of MRI delayed contrast enhancement to irreversible injury, infarct age, and contractile function," Circulation 100:1992-2002 (1999)). DE-MRI images are often obtained in a single breath-hold. DE-MRI can show sub-endocardial and other non-transmural infarcts (Wagner et al., "Contrast-enhanced MRI and routine single photon emission computed tomography (SPECT) perfusion imaging for detection of subendocardial myocardial infarcts: an imaging study," Lancet 361:374-379 (2003)), the identification of which has prognostic value.

Cine-MRI image frames are typically a set of single 2D slices acquired throughout the cardiac cycle, which can then be viewed in cine-mode. A single breath-hold is usually used. While non-tagged versions are often used alone, tagged versions show subendocardial contractility better and help discern true from apparent wall thickening due to through-slice motion. Both types of cine-MRI have an inherently low tissue contrast, however, so that non-viable myocardium is difficult to identify.

Image information from DE-MRI, which highlights non-viable myoeardium, and cine-MRI, which demonstrates myocardial wall motion, are used together to make the primary distinction between viable and non-viable myocardium. Abnormal myocardial wall motion with transmural hyper-enhancement indicates non-viable myocardium while abnormal myocardial wall motion with no hyper-enhancement represents viable tissue (ischemic, hibernating, stunned, or myopathic), the sub-types of which may be distinguished with first-pass perfusion MRI (rest and/or stress), stress cine-MRI, and clinical history. This standard MRI approach has been successfully validated against positron-emission-tomography (PET) (Klein et al., "Assessment of myocardial viability with contrast-enhanced magnetic resonance imaging-comparison with positron emission tomography," Circulation 105:162-167 (2002)) and single-photon-emission-computed-tomography (SPECT) (Wagner et al., "Contrast-enhanced MRI and routine single photon emission computed tomography (SPECT) perfusion imaging for detection of sub-endocardial myocardial infarcts: an imaging study," Lancet 361:374-379 (2003)) for the assessment of myocardial viability.

Both the cine-MRI and DE-MRI images can be acquired using a segmented process, in which different segments of the k-space of each image are acquired from different cardiac cycles but at approximately the same phase in each of the cycles. This allows a higher resolution image to be produced, as only a segment of the image must be captured from each cardiac cycle.

SUMMARY

The invention is able to highlight nonviable myocardium while simultaneously showing wall motion. This increases ease-of-interpretation and decreases overall scan time for myocardial viability evaluation using MRI.

In general the invention features a method of magnetic resonance imaging of anatomy that is subject to a movement cycle (e.g., the heart during a cardiac cycle), comprising: administering a magnetic resonance contrast agent; waiting a period of time until the contrast agent is effective to cause selected portions of the anatomy (e.g., dead cardiac tissue) to have a different T1 recovery rate from that of other portions (normal cardiac tissue); administering a plurality of inversion recovery pulses spaced in time; acquiring image data at a data acquisition time that is spaced in time by a known time interval following an inversion recovery pulse; varying the time within the movement cycle at which the inversion recovery pulses are administered so that the associated data acquisition times are at a plurality of phases of the movement cycle; processing image data acquired at a phase of the movement cycle to produce at least a portion of an image frame at that phase; and performing the processing for a plurality of phases of the movement cycle to produce a plurality of image frames corresponding to a plurality of phases.

Preferred implementations of the invention may incorporate one or more of the following: Selected portions and other portions of the anatomy may comprise cardiac or vascular tissue. Selected portions or the other portions of the anatomy may comprise blood within the heart or vasculature. The movement cycle may be the cardiac cycle. The anatomy being imaged may comprise cardiac vascular tissue. The inversion recovery pulses may be synchronized to the cardiac cycle. The inversion recovery pulses may be gated to the R wave of the cardiac cycle. The inversion recovery pulse may occur following a first R wave, and at least some of the data acquisition may occur following a second R wave, and thus in a different cardiac cycle than the inversion recovery pulse. The data acquisition occurring following a second R wave may be synchronized to the second R wave, and the processing of the image data may comprise retrospective gating of the acquired data. The data acquisition may bridge across an R wave, from one cardiac cycle to the next, and the association of data with the correct cardiac cycle may be accomplished retrospectively in the processing of the image data. The times at which the inversion recovery pulses are administered may be spaced in time by a fixed interval. The times at which the inversion recovery pulses are administered may be spaced in time by a varying interval. An inversion pulse may be administered generally in every other cardiac cycle. Acquiring image data may comprise using an FRSSE sequence. Acquiring image data may comprise using a spoiled-gradient-echo sequence. Data acquisition times may be spaced more closely in the systolic phase than in the diastolic phase. Additional image frames may be produced for the diastolic phase by interpolation. The invention may further comprise acquiring phase reference data during alternate cardiac cycles in which image data is not acquired, and using the phase reference data to perform phase-sensitive data acquisition. The known time interval may comprise a normal T1 for cardiac tissue in a population of patients. The known time interval may comprise a T1 determined for the specific patient undergoing imaging. The times of acquisition of lower spatial frequency image content may be closer to the known time interval following the inversion recovery pulse than are the times of acquisition of higher spatial frequency image content. Data may be acquired using segmented acquisition so that data acquired for an image frame comes from at least two cardiac cycles. Data may be acquired using parallel imaging. The invention may further comprise the use of tagged excitation. The data acquisition times may correspond approximately to the null time for normal cardiac tissue. The data acquisition times may correspond to times earlier or later than the null time for normal cardiac tissue. Multiple slices of data may be acquired simultaneously using phase encoding. The data acquisition time may comprise a data acquisition interval.

Among the many advantages of the invention (some of which may be achieved only in some of its various implementations) are the following.

Less time may be required for myocardial viability testing to be performed using MRI. If breath holds are used, the number of breath holds performed by the patient may be reduced.

An exact match of spatial orientation may be achieved by simultaneously acquiring and showing hyper-enhancing non-viable myocardium, nulled normal myocardium, and the corresponding wall motion all within the same image set. This may increase the reliability of subsequent interpretation by a physician as all spatially matched data is from the same acquisition, e.g., from the same single breath-hold.

The MRI images are easier for the diagnostician to interpret, as they eliminate the need for a mental synthesis of information from both acquisitions. There may be less need for reliance on physician memory and/or complex display technology. The former point, in particular, may help increase the reliability of subsequent interpretation by a physician.

Significantly reduced total scan time may increase patient comfort and compliance. Given that patients undergoing myocardial viability evaluation are typically chronically ill, this may likely increase the fraction of completed studies at an MRI center.

Reduced scan time may make myocardial viability MRI studies fiscally comparable to more common, shorter MRI examinations. This increases efficiency of equipment usage and patient throughput, and may permit more patients to be examined for myocardial viability per unit of time.

Among the many applications of the invention (some of which may be achievable only in some of its implementations) are the following:

Some implementations may be used for the assessment of myocardial viability in the patient being evaluated for possible revascularization surgery.

Some implementations may be used for the evaluation of myocardial masses with enhancing components. It is known that fibrous tissue such as scar tissue will demonstrate delayed hyper-enhancement—this is the premise of DE-MRI. Similarly, a cardiac-related mass or structure that contains fibrous tissue for other reasons or demonstrated delayed enhancement for other reasons could also be assessed with some implementations. Some implementations may be used, for instance, to demonstrate deformation of such a finding during the cardiac cycle or its dynamic effect on other structures during the cardiac cycle.

In addition to delayed-enhancement assessment of cardiac masses, first-pass or early arterial and/or venous enhancement patterns may be seen in cine-mode using some implementations, rather than only at a time of delayed enhancement.

Similarly, valvular tissue is made of fibrous connective tissue, and also demonstrates delayed enhancement properties. Some implementations may potentially be used, therefore, in the dynamic assessment of valves with delayed enhancement tissue contrast that would highlight the position and orientation of valves.

Other implementations, features, advantages, and applications of the invention will be apparent from the detailed description, drawings, and claims.

DESCRIPTION OF DRAWINGS

FIGS. 2A-2E are cardiac images comparing results achieved with an implementation of the invention to results achieved with prior art cine-MRI and delayed enhancement MRI techniques.

FIGS. 3A-3E are cardiac images comparing results achieved with an implementation of the invention to results achieved with prior art cine-MRI and delayed enhancement MRI techniques.

FIGS. 5A-5F are cardiac images achieved with an implementation of the invention.

DETAILED DESCRIPTION

There are a great many possible implementations of the invention, too many to describe herein. Some possible implementations that are presently preferred are described below. It cannot be emphasized too strongly, however, that these are descriptions of implementations of the invention, and not descriptions of the invention, which is not limited to the detailed implementations described in this section but is described in broader terms in the claims.

One implementation includes a class of pulse sequences that involves the combination of aspects of DE-MRI and cine-MRI.

One aspect of DE-MRI is an inversion pulse performed prior to data acquisition. This inversion pulse is used to null out normal myocardial signal in order to highlight hyper-enhancing myocardial tissue (non-viable myocardium). Data acquisition occurs at a consistent point in the cardiac cycle, usually late diastole.

One aspect of cine-MRI is acquisition of image data throughout the cardiac cycle over multiple heartbeats, which is subsequently organized into images of the heart at various time points throughout the cardiac cycle.

Some implementations combine these aspects through the use of (1) an inversion pulse per data acquisition for appropriate tissue contrast and (2) a series of acquisitions over a number of heartbeats with the time of data acquisition during the cardiac cycle being varied.

Figure 1:
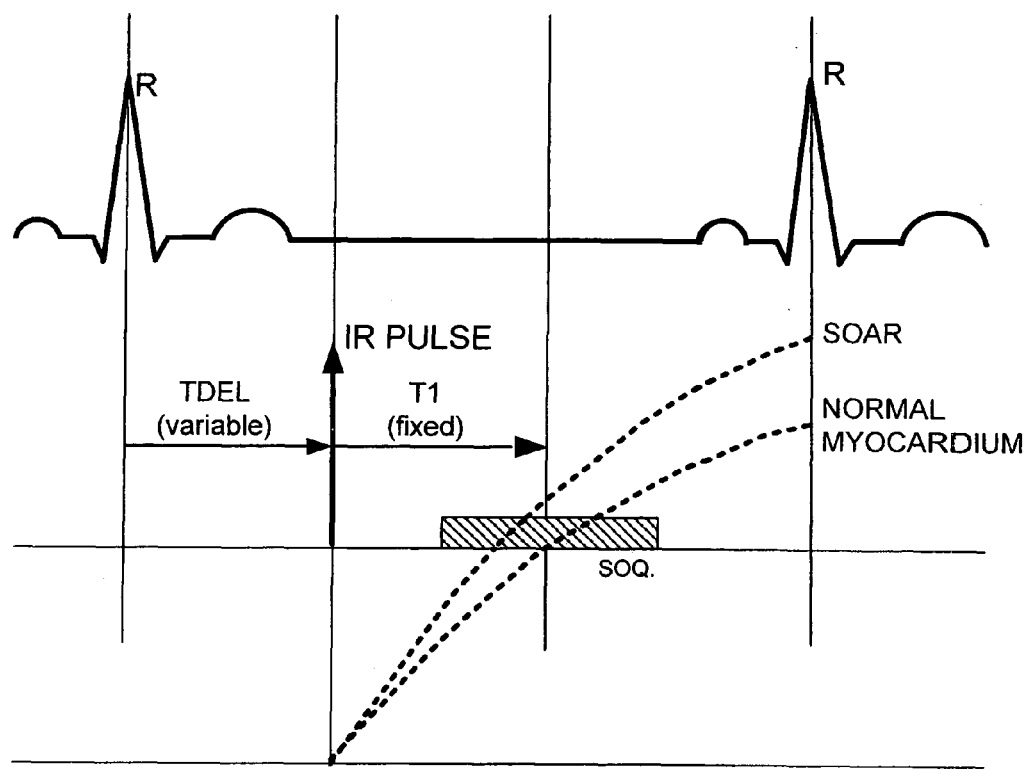
FIG. 1 is a timing diagram for some implementations of the invention, showing the relationship of an inversion recovery (IR) pulse to the R wave of a cardiac cycle.
Figure 6:
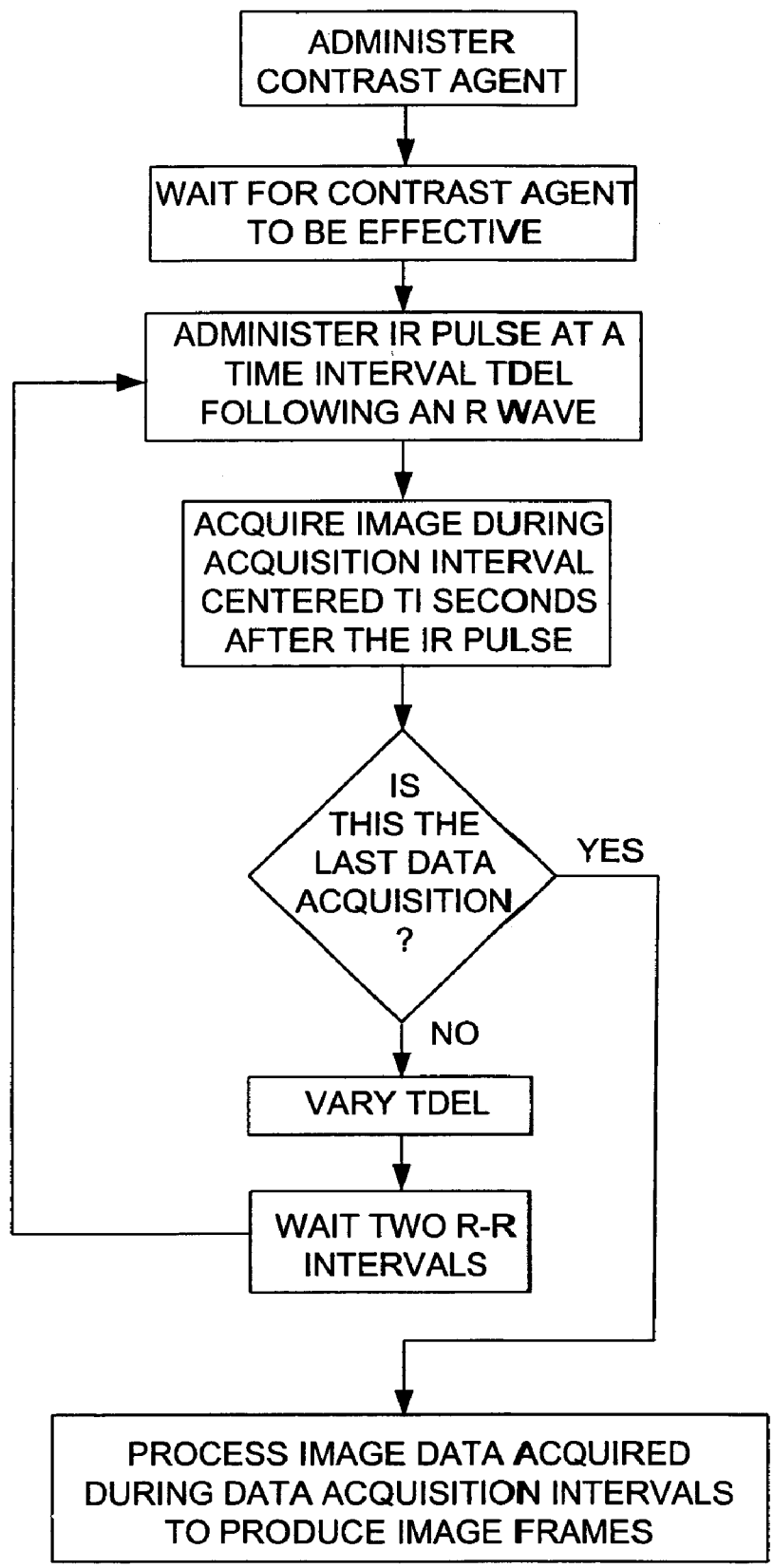
FIG. 6 is a flow diagram of the method used in some implementations of the invention.

The method used in these implementations (which we term scar-cine-MRI) is illustrated in the timing diagram of FIG. 1 and the flow diagram of FIG. 6. In this illustration, TDEL represents the time of the inversion recovery pulse (IR pulse) relative to the R peak of the electrocardiogram (ECG) signal of a patient. Data acquisition occurs at a known time interval (e.g., T1) after the IR pulse. In some implementations, T1 is set nominally to a typical value, e.g., 275 ms, at which time normal myocardial signal is nulled or nearly nulled in most patients. Data acquisition occurs over an acquisition interval using an acquisition train that collects all (or some in case of segmented acquisition) data for one image frame corresponding to the phase of the cardiac cycle at the time of data acquisition. Data collection during the acquisition interval can be organized so that data for lower order spatial frequencies is acquired near the null point of the IR pulse (T1 ms after the IR pulse), and data for higher spatial frequencies is collected at times further away from the null point. Additional images for other cardiac phases are made by performing the processing at other values of TDEL using the same TI.

Figure 7:
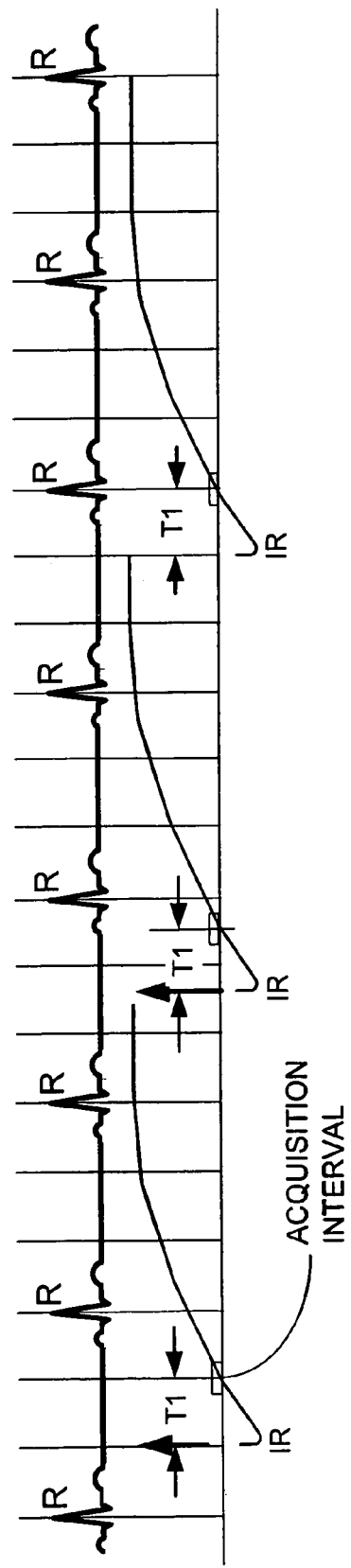
FIG. 7 is a timing diagram for some implementations showing the IR pulses and data acquisition for a plurality of cardiac cycles.

For example, TDEL may be incremented with a constant time interval, e.g., 70 ms, and one set of IR pulse and data acquisition may be performed for every two heartbeats (RR intervals). Acquiring data every other heart beat allows time for signal recovery before administration of a further IR pulse. In these implementations, if images from 12 cardiac phases are desired, then 24 RR intervals are used. Thus, for a patient with an average RR interval of 840 ms, TDEL is stepped at 70 ms increments and total scan time is 20 seconds. FIG. 7 shows the IR pulses and data acquisition intervals occurring over six of the cardiac cycles. The times at which the IR pulses are administered and data is acquired are shifted progressively later in the cardiac cycle. It is not necessary that the IR pulse times advance uniformly over time. Non-uniform changes in the time of administration could be used, and the order in which IR pulses are administered could be changed (e.g., pulses at later cardiac phases need not occur at earlier cardiac phases).

A Siemens Sonata 1.5T scanner was used for one implementation. A dedicated cardiac MRI scanner (Sonata, Siemens Medical Solutions, Erlangen, Germany) with short bore and high strength gradient coils was used. This implementation used a non-slice-selective inversion pulse, a T1 of 280 ms, a single complete acquisition train per cardiac phase, a fully-refocused-steady-state-excitation sequence basis (TrueFISP), a TR of 2.2 ms, an asymmetric echo, a TE of 1.1 ms, a bandwidth of 1400 Hz/mm, a variable field of view nominally set at 300 mm, and a variable acquisition matrix that was nominally set at 128×128. The number of cardiac phases and the time step interval could be varied depending on the patient's cardiac cycle duration. A nominal 12 cardiac phases and 50 ms time step interval was chosen, and then each parameter was varied to cover the cardiac cycle duration. Prospective gating was used.

Imaging of patients with known myocardial infarctions and a patient with a previously undiagnosed left ventricular fibroma was obtained approximately 20 minutes after injection of 40 ml of 0.5 mmol/ml gadopentetate dimeglumine (Magnevist, Berlex Imaging, Wayne N.J.).

Figure 2D:
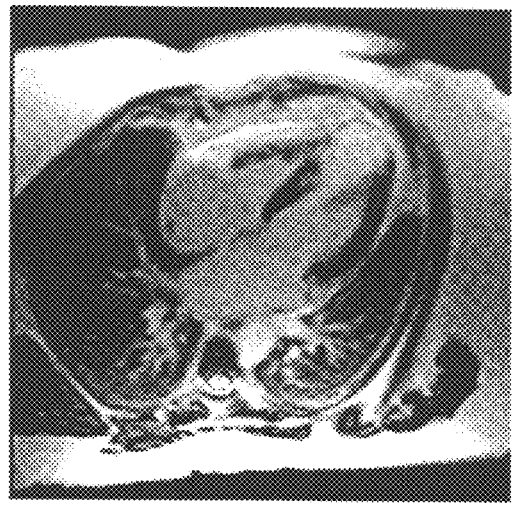
Figure 2E:
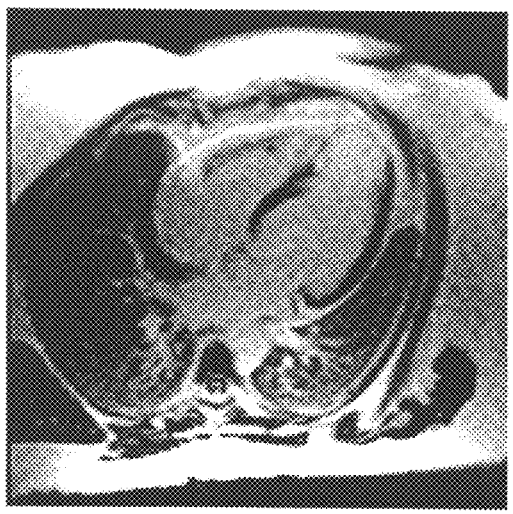
Figure 3A:
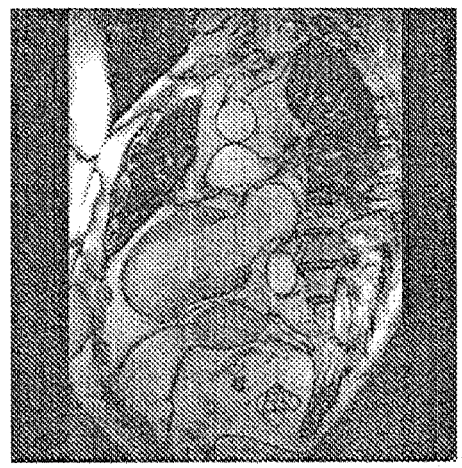
Figure 3B:
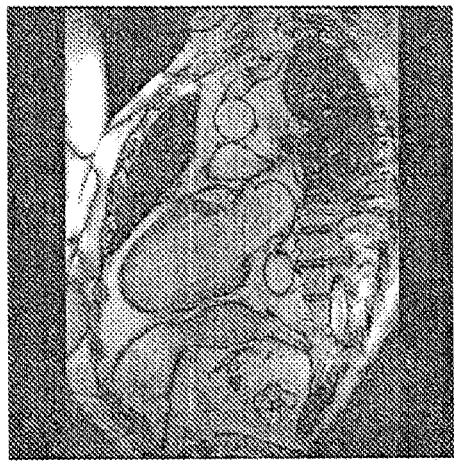
Figure 3C:
Figure 4A:
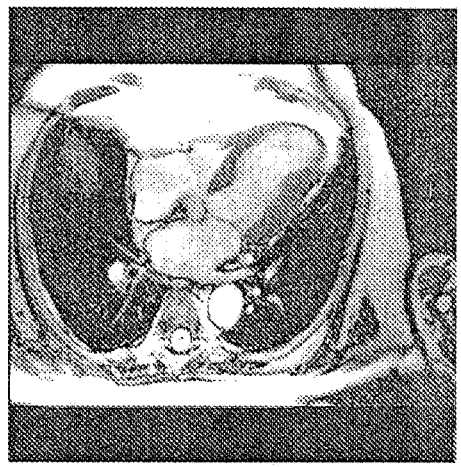
FIGS. 4A-4E are cardiac images comparing results achieved with an implementation of the invention to results achieved with prior art cine-MRI and delayed enhancement MRI techniques.
Figure 4B:
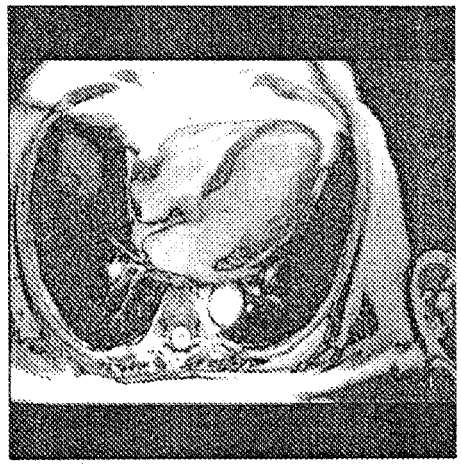
Figure 4C:
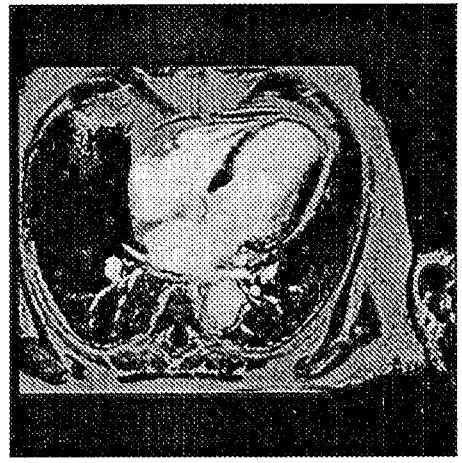
Figure 4D:
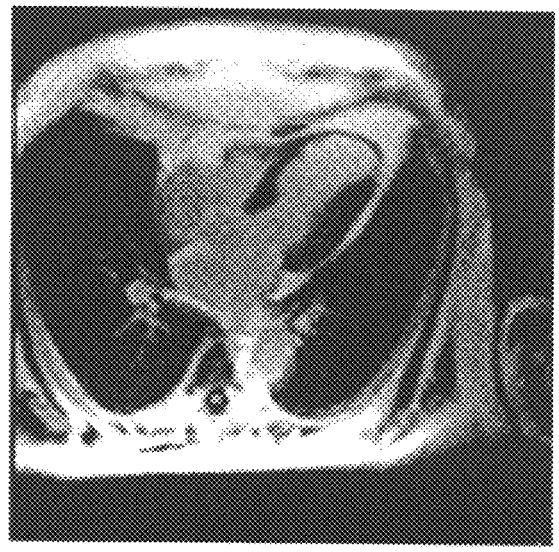
Figure 4E:
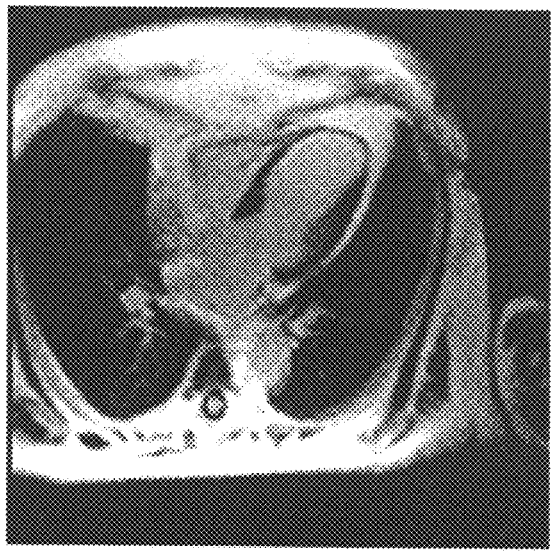

In FIGS. 2A-2E sample images from a myocardial viability examination are provided. The patient had a previous transmural apical infarction and distal septum. FIGS. 2A and 2B demonstrate end systolic and late diastolic four chamber images respectively from a typical cine-MRI sequence in this patient, demonstrating a thinned apex and distal septum with no associated wall motion. The rest of the myocardium demonstrated reduced wall motion. FIG. 2C is a four chamber delayed enhancement image demonstrating hyper-enhancement of the apex and distal septum corresponding to infarcted tissue. FIGS. 2D and 2E demonstrate corresponding 128×128 matrix scar-cine-MRI images in the four chamber orientation at end systole and late diastole. These images simultaneously demonstrate the presence of transmural non-viable tissue in the apex and distal septum (areas of hyper-enhancement) and both the lack of associated wall motion in these regions and the presence of wall motion in other myocardial regions. In this way, information from cine-MRI and DE-MRI may be presented from a single sequence.

In FIGS. 3A-3E and 4A-4E, more example images from a myocardial viability examination are provided. This patient had a previous sub-endocardial infarction of the distal anterior and septal regions with apical inferior involvement. Both two-chamber (FIG. 3) and four-chamber (FIG. 4) views are provided. These images demonstrate the lack of significant myocardial wall contraction in the involved areas while simultaneously showing the location of sub-endocardial infarction, as has been demonstrated for the patient in FIG. 2.

In FIGS. 5A-5F, example images from a patient with a large ventricular fibroma and moderate pericardial effusion are provided. Short axis and two chamber views are shown. Acquisition of cardiac phase data was begun in early diastole and stepped to late systole. Since a fibroma is made of fibrous tissue, it will demonstrate hyper-enhancement just like chronic scar tissue. The fibroma is located in the anterior wall of the left ventricle and demonstrates a central calcification (low signal intensity). Mild deformation of the fibroma is demonstrated during the cardiac cycle. The pericardial effusion initially demonstrates a high signal intensity on the first acquisition (early diastole image 1); this signal quickly reaches an equilibrium signal. This artifact is likely correctable with additional a priori excitations.

Many other implementations may be used, e.g., to improve performance in particular circumstances.

One possible implementation uses a spoiled-gradient-echo sequence. While either a fully-refocused-steady-state-excitation (FRSSE) or a spoiled-gradient-echo basis sequence (or other sequence types) may be used for data acquisition, FRSSE is usually preferred for its higher signal-to-noise ratio and shorter duration. Because FRSSE maintains magnetization on the transverse plane over multiple excitations, it is more prone to artifacts associated with magnetic field inhomogeneity. There may be circumstances, for instance, if magnetic field inhomogeneity is relatively high, where it would be preferable to use an alternative implementation that uses a spoiled-gradient-echo basis for data acquisition rather than FRSSE.

Another possible implementation provides improved cine imaging. In the implementation earlier described, the timing of the second R peak is assumed to occur at a fixed time after the first R peak, i.e., the patient's heart rate is stable. Data is collected relative to the first R peak. If a patient's heart rate varies during acquisition, the variable timing of the second R peak would affect the timing of acquisition relative to any data collected during the second R-R interval. Most data is collected during the first R-R interval (i.e., the same R-R interval in which the IR pulse is administered), but data in the early part of a cardiac cycle must typically be obtained during the second R-R interval (i.e., the next R-R interval after the IR pulse) due to the length of the inversion time (the time from inversion pulse to data acquisition is typically 275 ms). If the second R peak (between the first and second R-R interval) occurs at an unexpected time, this will typically affect data obtained during systole, and can create an uneven appearance to systolic motion. The robustness of cine quality may be improved by taking into account the actual timing of the second R peak relative to any data collected during the second R-R interval (e.g., by using retrospective gating).

On breath-hold scans, because the total scan time is limited to one-breath-hold (less than 30 seconds), it may also be beneficial to try to improve temporal resolution during systole relative to diastole. An implementation that addresses this issue would involve retrospective gating using knowledge of when the second R peak occurs for appropriate categorization of acquired data. Post-acquisition interpolation of data may then be performed in order to create even temporal resolution throughout the cardiac cycle.

Another implementation for addressing this issue would involve real-time rejection of acquired data if data happens to fall outside certain prescribed time windows relative to the second R peak. This would be followed by additional data acquisition to compensate for the rejected data acquisition.

Yet another implementation would decrease the time step interval when data is being collected during systole and increase the time step interval during diastole, and then use interpolation of data collected during diastole to establish an even temporal resolution throughout the cardiac cycle. For instance, the time step interval may be decreased to 30 ms during systole, and increased to 60 ms during diastole. Subsequent processing would interpolate images obtained during diastole to create missing image sets at 30 ms intervals throughout the cardiac cycle.

Phase sensitive reconstruction may be used in some implementations to reduce sensitivity to variation in optimal T1 values for nulling normal myocardium. Phase sensitive reconstruction has been used in other applications in the prior art (Kellman et al., "Phase-sensitive inversion recovery for detecting myocardial infarction using gadolinium-delayed hyper-enhancement," Magn. Reson. Med. 47:372-83 (2002)). The requirement of phase-sensitive-reconstruction that there be two R-R intervals per phase-sensitive-acquisition is readily met as many implementations typically already embody the 2 R-R requirement.

A long single-shot acquisition train may overlap more than one cardiac phase (e.g., as occurs in the third data acquisition shown in FIG. 7). To improve temporal resolution, a different structural implementation is possible in which view sharing is performed, whereby portions of different acquisition trains that correspond to the same cardiac phase would be reconstructed together after acquisition. No additional acquisition would be required as this is an entirely post-processing technique.

Another implementation would be to use parallel imaging to improve temporal resolution and/or scan time. Parallel imaging is a recently developed method of using multiple receiver coils to significantly reduce scan time by mathematical combination of image data or spatial frequency data from each coil (Griswold et al., "Generalized autocalibrating partially parallel acquisitions (GRAPPA)," Mag. Reson. Med. 47:1202-1210 (2002)).

Segmented image acquisition may be used to improve temporal resolution at the cost of scan time or fewer image frames. In segmented acquisition, data for a single image frame is acquired not from a single data acquisition but from multiple data acquisitions acquired at the same cardiac phase. For example, a 12 cardiac phase acquisition with a 2-segment acquisition would require data to be acquired from 24 cardiac cycles, each separated by a signal recovery cycle in which data is not acquired, for a total of 48 cycles. The acquisition would take 40 seconds in a patient with a 72 beat-per-minute heart rate. If fewer phases are desired, however, e.g., if 8 cardiac phases are desired, a corresponding 2 segment implementation would have a 27 second duration.

Other myocardial scars, e.g., other fibrous structures such as heart valve leaflets, can also be hyper-enhanced. Thus, one implementation could use a T1 value to null the signal from blood rather than from normal myocardium. In this manner, heart valve leaflets will be highlighted against a dark background for better evaluation.

Another implementation may use a gridded excitation in combination with scar-cine-MRI for better observation of wall motion. The grid that is formed may be dark, as typically done at the present time on tagged sequences, or may be bright, as a better highlight against a darker background.

It may be effective to obtain more than one slice at a time to obtain more spatial coverage per unit of time. Multi-slice, slab, or volume excitation/acquisition modifications may then be used.

There may be circumstances, for instance, during the characterization of the enhancement pattern of a cardiac mass, when it would be preferred to observe the mass in cine-mode during arterial/venous enhancement at a time prior to what would be considered delayed enhancement. Thus, not all implementations use delayed enhancement in the "conventional" sense of that term.

Many other implementations of the invention are possible, including, e.g., different combinations of the implementations disclosed.

What is claimed is:

1. A method of magnetic resonance imaging, comprising the steps of:
    administering a magnetic resonance contrast agent to a subject comprising anatomy that moves in a movement cycle comprising an identifiable movement characteristic in each cycle;
    waiting a period of time after administering said magnetic resonance contrast agent until the contrast agent causes a first portion of the anatomy to have a different T1 recovery time from a T1 recovery time of other, second portions of the anatomy;
    after said period of time, implementing a plurality of magnetic resonance data acquisition sequences to acquire magnetic resonance data from the anatomy, each of said magnetic resonance data acquisition sequences having a time duration that is less than at least one of said movement cycles;
    in each of said magnetic resonance data acquisition sequences, activating an inversion recovery pulse and beginning acquisition of said magnetic resonance data from the anatomy at a predetermined time following activation of the inversion recovery pulse;
    in each of said magnetic resonance data acquisition sequences, activating the inversion recovery pulse at a different time with respect to the identifiable movement characteristic of the at least one movement cycle encompassed by the respective magnetic resonance data acquisition sequence, and thereby acquiring a plurality of magnetic resonance data sets respectively from the plurality of magnetic resonance data acquisition sequences; and defining an interval between occurrences of said identifiable movement characteristic in successive movement cycles;

in at least some of said plurality of magnetic resonance data acquisition sequences, both activating said inversion recovery pulse and acquiring said magnetic resonance data within the same interval; and processing said plurality of magnetic resonance data sets to produce, respectively therefrom, a plurality of images of the anatomy respectively at different phases in said movement cycle, with said first portion appearing visually differently in the respective different phases due to the different times of activation of the inversion recovery pulse in the respective magnetic resonance data acquisition sequences.

2. The method of claim 1 wherein one or more of the first and the other, second portions of the anatomy comprise cardiac or vascular tissue.

3. The method of claim 1 wherein one or more of the first and the other, second portions of the anatomy comprise blood within the heart or vasculature.

4. The method of claim 1 wherein the movement cycle is the cardiac cycle and said interval is the R-R interval.

5. The method of claim 4 wherein data acquisition times are spaced more closely in a systolic phase of the cardiac cycle than in a diastolic phase of the cardiac cycle.

6. The method of claim 5 further comprising producing additional image frames for the diastolic phase by interpolation.

7. The method of claim 4 further comprising acquiring phase reference data during alternate cardiac cycles in which image data is not acquired, and using the phase reference data to perform phase-sensitive data acquisition.

8. The method of claim 4 wherein the known time interval comprises a normal T1 for cardiac tissue in a population of patients.

9. The method of claim 4 wherein the predetermined time comprises a T1 time determined for the subject.

10. The method of claim 4 wherein the image data is acquired using segmented acquisition so that data acquired for an image frame comes from at least two cardiac cycles.

11. The method of claim 4 wherein the image data is acquired using parallel imaging.

12. The method of claim 4 wherein the data acquisition times correspond approximately to null time for normal cardiac tissue.

13. The method of claim 4 wherein the data acquisition times correspond to times earlier or later than null time for normal cardiac tissue.

14. The method of claim 4 further comprising:

for image data corresponding to an early portion of the cardiac cycle, causing a second set of the inversion recovery pulses having associated second set of data acquisition times to be administered so that for at least one of the second set of the inversion recovery pulses administered in a first R-R interval an associated one of the second set of data acquisition times occurs during a second R-R interval following the first R-R interval; and processing image data acquired at the plurality of phases of the cardiac cycle including processing the image data acquired during the second set of data acquisition times to produce a plurality of image frames corresponding to the plurality of phases.

15. The method of claim 1 wherein the anatomy being imaged comprises cardiac vascular tissue.

16. The method of claim 15 wherein the inversion recovery pulses are synchronized to cardiac cycles.

17. The method of claim 16 wherein at least one of the inversion recovery pulses is gated to a first R wave of a first cardiac cycle.

18. The method of claim 17 wherein the at least one of the inversion recovery pulses occur following the first R wave, and at least some of the data acquisition associated with the at least one of the inversion recovery pulses is activated following a second R wave of a second cardiac cycle, the second cardiac cycle being different from the first cardiac cycle.

19. The method of claim 18 wherein the data acquisition occurring following the second R wave is synchronized to the second R wave, and the processing of the image data comprises retrospective gating of the acquired data.

20. The method of claim 17 wherein the data acquisition associated with the at least one of the inversion recovery pulses bridges across a second R wave, from the first cardiac cycle to a next cardiac cycle, and the association of data with a correct cardiac cycle is accomplished retrospectively in the processing of the image data.

21. The method of claim 15 wherein an inversion pulse is activated generally in every other cardiac cycle.

22. The method of claim 1 wherein said times at which the inversion recovery pulses are activated are spaced in time by a fixed interval.

23. The method of claim 1 wherein said times at which the inversion recovery pulses are activated are spaced in time by a varying interval.

24. The method of claim 1 comprising implementing a fully refocused steady state excitation sequence as each of said plurality of magnetic resonance data acquisition sequences.

25. The method of claim 1 comprising implementing a spoiled-gradient-echo sequence as each of said plurality of magnetic resonance data acquisition sequences.

26. The method of claim 1 comprising, in each magnetic resonance data acquisition sequence, acquiring magnetic resonance data with a lower spatial frequency image content at times closer to the predetermined time following the inversion recovery pulse than times of acquisition of magnetic resonance data with higher spatial frequency image content.

27. The method of claim 1 further comprising using tagged excitation in producing the image data.

28. The method of claim 1 wherein multiple slices of the image data are acquired simultaneously.

29. The method of claim 1 wherein the data acquisition times comprise data acquisition intervals.

* * * * *